United States Patent [19]

Brouwer et al.

[11] Patent Number: 5,134,145

[45] Date of Patent: Jul. 28, 1992

[54] PESTICIDAL PYRIMIDINYL BENZOIC ACIDS AND ESTERS

[75] Inventors: Walter G. Brouwer, Guelph; Ethel E. Felauer, Puslinch, both of Canada; Paul T. McDonald, Middlebury, Conn.

[73] Assignees: Uniroyal Chemical Company, Inc., Middlebury, Conn.; Uniroyal Chemical Ltd./Ltee, Elmira, Canada

[21] Appl. No.: 438,913

[22] Filed: Nov. 17, 1989

[51] Int. Cl.$^5$ .................. C07D 239/54; A01N 43/54
[52] U.S. Cl. .................... 514/274; 544/311; 544/313; 544/314
[58] Field of Search ............... 514/274; 544/311, 314, 544/313

[56] References Cited

U.S. PATENT DOCUMENTS

| | | | |
|---|---|---|---|
| 4,280,999 | 7/1981 | Steelman et al. | 424/251 |
| 4,394,383 | 7/1983 | Kawata | 424/285 |
| 4,746,352 | 5/1988 | Wenger et al. | 71/90 |
| 4,760,163 | 7/1988 | Wenger et al. | 560/34 |
| 4,954,635 | 9/1990 | Rosario-Jansen | 548/354 |
| 4,988,719 | 1/1991 | Wagner | 514/369 |

OTHER PUBLICATIONS

Wenger et al., Chemical Abstracts, vol. 109, entry 231048g (1988).

Primary Examiner—John M. Ford
Attorney, Agent, or Firm—Glenn E. Karta

[57] ABSTRACT

This invention is related to a novel class of aryl pyrimidine derivatives having insecticidal, miticidal and nematocidal activity at low concentration. The class of compounds is represented by formula (I):

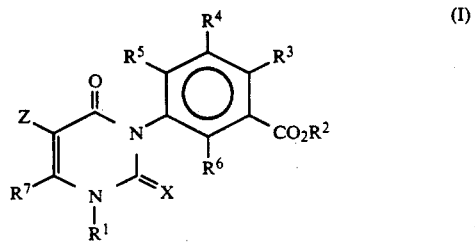

wherein $R^1$, $R^2$, $R^3$, $R^4$, $R^5$, $R^6$, X and Z have the significance given in the description.

Pesticidal compositions, methods of controlling pests and methods for preparing the compounds are within the scope of the invention.

8 Claims, No Drawings

PESTICIDAL PYRIMIDINYL BENZOIC ACIDS AND ESTERS

BACKGROUND OF THE INVENTION

1. Field of the Invention

The present invention is directed to a class of aryl pyrimidines and derivatives thereof. More specifically, the present invention is directed to a class of phenyl pyrimidine derivatives useful as insecticides, miticides and nematocides, particularly useful against rice planthopper.

2. Description of Related Art

Commercially important food, fiber and ornamental plants are continually subjected to the devastation caused by insect, mite and nematode pests. This represents a serious economic threat, particularly to such important grain plants as rice and corn. For this reason there is a continuing need for the development of new more effective insecticides, miticides and nematocides, especially ones that are effective at low dosages. Such pesticides combine the necessary control of insects, mites and nematodes without attendant environmental difficulties.

The utilization of aromatic substituted pyrimidines having insecticidal properties is well known in the art. One such disclosure in U.S. Pat. No. 4,280,999, which describes 5-chloro-3-phenyl-6-methyluracil as having insecticidal properties against certain insect pests. Most of the chemicals disclosed in this patent possess alkyl substitution at position 3 of the pyrimidine ring and biological data is only given for a single alkylated compound, i.e., 5-bromo-3-sec-butyl-6-methyl uracil. Specifically, U.S. Pat. No. 4,280,999 discloses that insects of the family Culicidae, e.g., mosquitoes are controlled at relatively high dosage rates.

U.S. Pat. No. 4,746,352 and its divisional, U.S. Pat. No. 4,760,163, disclose certain 3-(5-carboxy-4-(halo or nitro substituted)-phenyl) uracil esters and salts having herbicidal properties. Insecticidal activity is not disclosed.

A new class of compounds have now been discovered which have particular pesticidal application as insecticides, miticides and nematocides being particularly effective against pests which attack commercially important grain plants, but which are so active that they can be applied in low concentrations.

SUMMARY OF THE INVENTION

A novel class of pyrimidinyl benzoic acids and esters having outstanding insecticidal, miticidal and nematocidal activity, particularly against rice plant hoppers; methods for preparing same; and pesticidally active compositions containing same are disclosed. The compounds are represented by the formula:

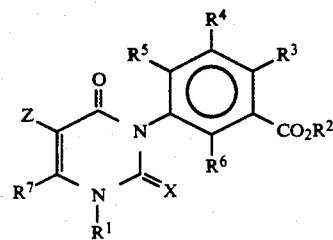

(I)

wherein the substituents $R^1$ through $R^7$ inclusive, X and Z are as hereinafter described.

DETAILED DESCRIPTION OF THE INVENTION

The invention relates to insecticidally, miticidally and nematocidally active compounds of the formula:

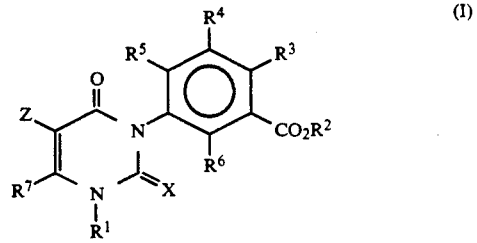

(I)

wherein $R^1$ is hydrogen, alkali or alkaline earth metal or organic base salts;

$R^2$ is i) hydrogen; alkali or alkaline metal salt; organic base salt; $C_1$-$C_6$ hydrocarbyl;

ii) —$RU_p$ wherein R is $C_1$-$C_6$ hydrocarbyl residue, U is halogen and p is an integer which cannot exceed the number of hydrogen atoms of the completely hydrogenated hydrocarbyl moiety;

iii) —$ROR^8$ wherein R is $C_1$-$C_6$ hydrocarbyl and $R^8$ is $C_1$-$C_4$ alkyl;

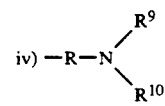

wherein R is $C_1$-$C_6$ hydrocarbyl and $R^9$ and $R^{10}$ are each independently hydrogen or $C_1$-$C_4$ alkyl;

v) —$R$—$CO_2R^{11}$ wherein R is $C_1$-$C_6$ hydrocarbyl and $R^{11}$ is $C_1$-$C_4$ alkyl;

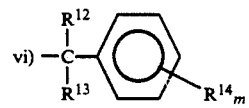

wherein $R^{12}$ and $R^{13}$ are each independently hydrogen, cyano or $C_1$-$C_2$ alkyl, $R_m^{14}$ is each independently, for m of 1 to 5, $C_1$-$C_4$ alkyl, $C_1$-$C_4$ alkoxy, halo or nitro and m is 0,1,2,3,4 or 5;

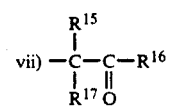

wherein $R^{15}$, $R^{16}$ and $R^{17}$ are each independently hydrogen or methyl; and viii) $-CH_2-\underset{O}{\triangleleft}$;

$R^3$ is hydrogen, halogen, nitro $C_1-C_6$ hydrocarbyl, $C_1-C_6$ alkoxy, $C_1-C_6$ alkylthio or $C_3-C_6$ cycloalkyl;

$R^4 R^5$ and $R^6$ are each independently hydrogen, halogen, $C_1-C_4$ alkyl or $-CO_2R^{18}$ wherein $R^{18}$ is $C_1-C_4$ alkyl;

$R^7$ is $C_1-C_6$ halogenated hydrocarbyl residue;

X is oxygen or sulfur; and

Z is hydrogen or halogen.

By hydrocarbyl is meant a linear, branched or cyclic, saturated or unsaturated moiety containing only hydrogen and carbon atoms.

Preferably, $R^1$ is hydrogen or potassium;

$R^2$ is hydrogen or $C_1-C_6$ hydrocarbyl;

$R^3$ is hydrogen, $C_1-C_4$ alkyl, $C_1-C_4$ alkoxy or $C_1-C_4$ thioalkyl;

$R^4$, $R^5$ and $R^6$ are hydrogen;

$R^7$ is $C_1-C_3$ fluorinated alkyl;

X is oxygen; and

Z is hydrogen.

Most preferably, $R^1$ is hydrogen or potassium;

$R^2$ is ethyl, methyl or isopropyl;

$R^3$ is methyl;

$R^4$, $R^5$ and $R^6$ are hydrogen;

$R^7$ is trifluoromethyl;

X is oxygen; and

Z is hydrogen.

In another aspect, this invention relates to insecticidal, miticidal and nematocidal compositions (hereinafter pesticidal compositions) comprising:

(A) a pesticidally effective amount of a compound having the structure of formula (I); and (B) a suitable carrier.

In yet another aspect, this invention relates to a method of controlling insects, mites and nematodes, which method comprises applying to the locus a pesticidally effective amount of a composition comprised of:

(A) a pesticidally effective amount of a compound having a structure in accordance with formula (I), and (B) a suitable carrier.

In a further aspect, this invention relates to a process for preparing a compound of formula (I) wherein $R^1$ through $R^{18}$, U, X, m, p and Z have the meanings given for formula (I), which process comprises the following retro-synthetic scheme:

$$NaHN-\underset{\underset{R^7}{|}}{C}=\underset{\underset{Z}{|}}{C}-C(O)OC_2H_5 + XCN-\bigcirc_{Q_1} \longrightarrow$$

(II)          (III)

(Ia)

A suitable sodium salt of an enamine (II) is reacted with an isocyanate or isothiocyanate (III) at low temperature, typically between $-50°$ C. and $-70°$ C. in an inert solvent such as tetrahydrofuran or dimethylformamide and the reaction allowed to come to ambient temperature over several hours. The pyrimidine (Ia) is isolated by first removing the solvent, dissolving the residual mixture in water and acidifying with mineral acid.

The class of compound represented by (II) are made by methods known in the literature. Starting materials are beta-keto esters which furnish the enamines by reaction with ammonia gas. Their sodium salts are made by adding the enamines to a suspension of sodium hydride in a suitable solvent like tetrahydrofuran or dimethylformamide.

$$R^7COCH(Z)C(O)OC_2H_5 \xrightarrow{NH_3}$$

(v)

$$R^7C(NH_2)=C(Z)C(O)OC_2H_5 \xrightarrow{NaH}$$

(vi)

$$NaHN-\underset{\underset{R^7}{|}}{C}=\underset{\underset{Z}{|}}{C}-C(O)OC_2H_5$$

(II)

wherein $R^7$, X and Z are as defined above and $Q_1$ represents the substitution pattern on the aromatic ring of structure formula (I).

The isocyanates and isothiocyanates of type (III) are made separately by reacting a suitable aromatic amine IV) with phosgene or thiophosgene.

$$H_2N-\bigcirc_{Q_1} \xrightarrow[\text{or}]{COCl_2} XCN-\bigcirc_{Q_1}$$

(IV)          (III)

Organic base salts are made by treating the compounds of formula (I), $R^1=H$ with an organic base of the formula R' R" R''' N, wherein one of the R', R" and R''' is a hydrocarbyl or hydroxyalkyl group having from 1 to 24 atoms, or two or three of the R' R" and R''' groups form a basic nitrogen-containing heterocyclic moiety, and the remaining substituents are hydrogen, in a suitable solvent, e.g., alcohol or tetrahydrofuran. In general, the organic base has to have sufficient strength to form a salt, i.e., the pKa of the base has to be greater than about 4.85. Removal of the solvent leaves the organic base salt of the compounds of the invention, that is

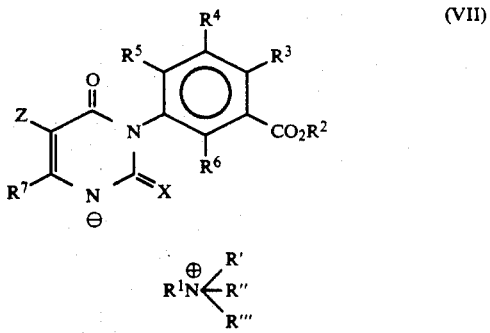

(VII)

The pesticidal compositions of the present invention, as stated above, employ compounds of structural formula (I) in combination with a carrier. The carriers, may be a finely divided or granular organic or inorganic inert material. Among the inert carriers are attapulgate clay, sand, vermiculite, corncobs, activated carbon and mineral silicates such as mica, talc, pyrophyllite and clays.

In another preferred embodiment, the composition comprises a solution. That is, the active agent, a compound whose structural formula is (I), is dissolved in a suitable solvent which acts as the carrier. Among the solvents, acting as carrier, are acetone, methanol, isopropanol, t-butyl alcohol, cyclohexanol, n-butyl alcohol, cyclohexanone, toluene, xylene, dioxane, methylformamide, dimethylsulfoxide, ethylene dichloride and N-methylpyrrolidone.

In still another preferred embodiment the composition comprises a water emulsion carrier. The emulsion is prepared from a solution as described immediately above. To the solution is added a surface active agent. Surface active agents suitable for use in forming the emulsion are known to those skilled in the art. McCutcheon's Detergents and Emulsifiers, Allured Publishing Corp., Ridgewood, N.J. (1970); U.S. Pat. No. 2,514,916, Columns 2 to 4; and, U.S. Pat. No. 2,547,734, Columns 3 and 4 provide detailed examples of such surface active agents. These agents may be anionic, non-ionic or cationic.

In yet still another preferred embodiment the composition employs a dispersant as carrier. In this embodiment, a compound of structural formula (I), is mixed with a solvent of the type described above to form a solution which is added to one of the above-described surface active agents and water.

In still another embodiment, the active compound is premixed with an inert solid carrier which is added to a surface active agent with water to provide another form of dispersion.

The above embodiment may alternatively be employed in non-liquid form. That is, the composition may take the form of a dust, granules, a paste or a wettable powder. In these embodiments, the active compound having the structural formula (I), is admixed with the inert carrier to form a solid composition. Thus, for example in the embodiment wherein a powder is formed, the solid inert carrier is provided in powder form. In many such cases, the inert carrier is a mineral silicate. The solid may be made wettable by the addition of a surface active agent.

In another principal application, an aerosol is prepared by dissolving the active compound in a first solvent. This first solvent is conventional in the sense that although it is volatile, it is not highly volatile. This solution is then admixed with a highly volatile solvent, a so-called liquid aerosol carrier. The aerosol carrier is liquid only under elevated pressure. At ordinary temperatures and at atmospheric pressure the aerosol carrier is a gas. In a sub-embodiment of this preferred embodiment the aerosol carrier may itself be active. For example the carrier may be an insecticide, a herbicide, a bactericide or a plant growth regulant.

In a preferred embodiment of a method of the present invention, a method for controlling insects, the insects particularly amenable to control by a compound having the structural formula (I), are green peach sphids, *Myzus persicae,* greenbugs, *Schizaphis graminum* and rice planthopper. *Sogatodes oryzicola.* Of these, control of rice planthoppers by compounds of the present invention have been found to be extremely effective at low dose rates.

The following examples are given to illustrate the scope of the present invention. Because these examples are given for illustrative purposes only, the invention embodied herein should not be limited to the actual examples provided.

EXAMPLE 1

Preparation of 1-methylethyl 5-[3,6-dihydro-2,6-dioxo-4-(trifluoromethyl)-1(2H)-pyrimidinyl]-2-methylbenzoate (Compound No. 1)

2-methyl-5-nitrobenzoic acid (52 g., 0.28 mol) is added in portions to thionyl chloride (30 ml) and slowly brought to reflux and held for 8 hours. Excess thionyl chloride was removed followed by addition of isopropyl alcohol (50 ml) and heating for 2 hours. Removal of excess alcohol gave crude ester which was reduced by adding dropwise to a mixture of iron powder (200 mesh, 56 g.), ethanol (160 ml), water (37 ml) and concentrated hydrochloric acid (4 ml) at 70° C. Stirring was employed. After the addition, the reaction was refluxed for 30 minutes before filtering hot. The iron oxide cake was washed with hot ethanol and the combined ethanol extracts were evaporated. The crude product was taken up in ethyl acetate washed with aqueous sodium bicarbonate, washed with water, dried over $MgSO_4$ and evaporated. Residual amber oil was distilled to give 1-methylethyl 5-amino-2-methylbenzoate, a clear oil, b.p. 92°–102° C./0.05 mm. This aniline (30 g.) in ethyl acetate (75 ml was added dropwise to a saturated solution of phosgene in ethyl acetate. During the addition, stirring was employed, phosgene was bubbled in continuously and the temperature allowed to rise. At the end of the addition, external heat was applied in order to attain reflux. After approximately 30 minutes, phosgene addition was stopped and ethyl acetate was removed by distillation at atmospheric pressure to approximately half volume. The remainder of the solvent was removed under reduced pressure. The residue was distilled to give 1-methylethyl 5-isocyanato-2-methylbenzoate, a clear oil, b.p. 90°–95° C./0.06 mm. Ethyl 4,4, 4-trifluoro-3-oxobutanoate (100 g.) was stirred and heated to 70° C. while ammonia gas was introduced for 30 minutes by which time 10.3 g. of ammonia had been absorbed. Addition of ammonia was stopped and the reaction was heated to 95° C. for two hours. Cooling produced two layers of liquid, the lower was removed and dried over molecular sieves overnight. After filtering, the product was distilled, b.p. 49°–58° C./15 mm (72.9 g.) of ethyl 3-amino-4,4,4-trifluoro-2-butenoate. This ethyl 3-amino-4,4,4-trifluoro-2-butenoate (31.8 g.) was added dropwise to a stirred suspension of sodium hydride (7.3 g., 60%) in dry tetrahydrofuran (275 ml) at 10° C. After the addition, the reaction mixture was cooled to −70° C. in an acetone/dry ice bath whereupon 1-methylethyl-5-isocyanato-2-methylbenzoate (38 g.) was added dropwise over 5–10 minutes, by which time the temperature had risen to −58° C. before cooling. The reaction was allowed to come slowly to ambient temperature and left overnight. Solvent was removed from the reaction under reduced pressure and the residue taken up in water (500 ml). After washing with ether, the solution was acidified with 2N hydrochloric acid. Crude product oiled out and solidified. This solid was collected in a filter, washed with water and dried. Recrystallization for isopropyl alcohol gave a white solid, m.p. 200°–202° C., 1-methylethyl 5-[3,6-dihydro-2,6-dioxo-4-(trifluoromethyl)-1(2H)-pyrimidinyl]-2-methylbenzoate, 22.6 g. A satisfactory IR NMR and CHN analysis was obtained.

EXAMPLE 2

Preparation of 1-methylethyl 5-(3,6-dihydro-2,6-dioxo-5-fluoro-4-trifluoromethyl)-1(2H)-pyrimidinyl]-2-methylbenzoate (Compound No. 6)

Ethyl 2,4,4,4-tetrafluoro-3-oxobutanoate (81 g.) in toluene (60 ml) was stirred and heated to 70° C. whereupon ammonia gas was bubbled in until an uptake of 6.8 g. was recorded. The reaction was then set for reflux and water removed azeotropically. Approximately 10 ml of water was removed. After cooling, the solvent was removed under reduced pressure and the residue distilled to give ethyl 3-amino-2,4,4,4-tetrafluoro-2-butenoate b.p. 79°–86° C./20 mm, 44 g.

This ester (7.2 g.) in tetrahydrofuran (50 ml) was added dropwise to a stirred suspension of sodium hydride (1.4 g., 60%) in tetrahydrofuran (75 ml) cooled (5° C.) in an ice bath. When the addition was complete, the reaction was cooled to −70° C. using an acetone/dry ice bath. 1-methylethyl 5-isocyanato-2-methylbenzoate (7.8 g.) in tetrahydrofuran (50 ml) was added and after two hours allowed to come to ambient temperature overnight. The solvent was removed under reduced pressure and the residue taken up in water, washed with ether and acidified. A yellow oil separated out. This oil was extracted into methylene chloride, washed with water, dried, filtered and evaporated to leave an oil which crystallized. Recrystallization from isopropyl alcohol gave white crystals of 1-methylethyl 5-[3,6-dihydro-2,6-dioxo-5-fluoro-4-(trifluoromethyl)-1(2H)-pyrimidinyl]-2-methylbenzoate, m.p. 97°–100° C., 3.0 g. Satisfactory analysis was obtained on this compound.

EXAMPLES 3–28

Preparation of Compound Nos. 2–5 and 7–28

A summary of the compounds prepared, including Compound Nos. 1 and 6 are shown in Table I. The compound is defined by its structure and melting point if the compound is a solid at room temperature and by its NMR if it is a glass or gum.

TABLE 1

| Cmpd. No. | R1 | R2 | R3 | R4 | R5 | R6 | R7 | X | Z | MP °C. |
|---|---|---|---|---|---|---|---|---|---|---|
| 1 | H | CH(CH$_3$)$_2$ | CH$_3$ | H | H | H | CF$_3$ | O | H | 200–202 |
| 2 | H | CH$_3$ | CH$_3$ | H | H | H | CF$_3$ | O | H | 203–206 |
| 3 | H | CH(CH$_2$CH$_3$)$_2$ | CH$_3$ | H | H | H | CF$_3$ | O | H | 175–178 |
| 4 | K | CH(CH$_3$)$_2$ | CH$_3$ | H | H | H | CF$_3$ | O | H | Glass[1] |
| 5 | H | CH$_3$ | H | H | H | H | CF$_3$ | O | H | 196–198 |
| 6 | H | CH(CH$_3$)$_2$ | CH$_3$ | H | H | H | CF$_3$ | O | F | 97–100 |
| 7 | H | CH$_3$ | OCH$_3$ | H | H | H | CF$_3$ | S | H | 258–262 |
| 8 | H | CH(CH$_3$)$_2$ | H | H | H | H | CF$_3$ | O | H | 182–184 |
| 9 | H | CH$_3$ | OCH$_3$ | H | H | H | CF$_3$ | O | H | 247–250 |
| 10 | H | CH$_3$ | OCH(CH$_3$)$_2$ | H | H | H | CF$_3$ | O | H | 192–194 |
| 11 | H | CH(CH$_3$)$_2$ | Cl | H | Cl | F | CF$_3$ | O | H | 72 |
| 12 | H | H | CH$_3$ | H | H | H | CF$_3$ | O | H | 284–287 |
| 13 | H | CH$_3$ | H | CO$_2$CH$_3$ | H | H | CF$_3$ | O | H | 209–210 |
| 14 | H | CH$_3$ | OCH(CH$_3$) | H | H | H | CF$_3$ | O | H | 139–140 |
| 15 | H | C$_2$H$_5$ | CH$_3$ | H | H | H | CF$_3$ | O | H | 160–161 |
| 16 | H | CH(CH$_3$)$_2$ | OCH$_3$ | H | H | H | CF$_3$ | O | H | 103–105 |
| 17 | H | CH$_3$ | OCH$_2$C≡CH | H | H | H | CF$_3$ | O | H | 152-6 |
| 18 | H | C$_2$H$_5$ | CH3 | H | H | H | C$_2$F$_5$ | O | H | Glass[2] |
| 19 | H | C$_2$H$_5$ | CH$_3$ | H | H | H | C$_3$F$_7$ | O | H | Glass[3] |
| 20 | H | nC$_3$H$_7$ | CH$_3$ | H | H | H | CF$_3$ | O | H | 202–205 |
| 21 | H | nC$_4$H$_9$ | CH$_3$ | H | H | H | CF$_3$ | O | H | 199–200 |
| 22 | H | CH$_2$CH=CH$_2$ | CH$_3$ | H | H | H | CF$_3$ | O | H | 193–194 |
| 23 | H | CHCN \| C$_6$H$_4$3-OC$_6$H$_5$ | CH$_3$ | H | H | H | CF$_3$ | O | H | Gum[4] |
| 24 | HN(C$_2$H$_5$)$_3$ | C$_2$H$_5$ | CH$_3$ | H | H | H | CF$_3$ | O | H | 106–108 |
| 25 | H | C$_2$H$_5$ | SC$_2$H$_5$ | H | H | H | CF$_3$ | O | H | 175–180 |
| 26 | K | K | CH$_3$ | H | H | H | CF$_3$ | O | H | >250 |
| 27 | H | C$_2$H$_5$ | CH$_3$ | H | H | H | CF$_3$ | S | H | 169–174 |
| 28 | H | CH(CH$_3$)$_2$ | F | H | H | H | CF$_3$ | O | H | 264–267 |

NMR DATA

| Cmpd. No. | |
|---|---|
| 4 | 0.9–4.4(m, 2xCH$_3$), 2.9(s, CH$_3$), 4.8–5.3(q, CH), 5.7(s, CH), 7.0–7.6(m, 3xH's) |
| 18 | 1.2–1.5(t, CH$_3$), 2.7(s, CH$_3$), 4.1–4.5(q, CH$_2$) 6.2(s, CH), 7.1–7.9(m, 3xH's), 10.0–11.2(s, NH) |
| 19 | 1.2–1.5(t, CH$_3$), 2.7(s, CH$_3$) 4.1–4.5(q, CH$_2$), 6.2(s, CH), 7.2–7.8(m, 3xH's), |

TABLE 1-continued

| | |
|---|---|
| | 10.0–10.3(s, NH). |
| 23 | 2.6(s, CH$_3$), 6.3–(s, CH) 6.8–7.9(m, 12xH's) |

EXAMPLE 13

Preparation of Insecticidal Compositions

Each of Compounds Nos. 1–28 were formed into compositions. This was accomplished by dissolving 0.3 g. of each of the compounds in 10 ml of acetone to which was added four drops of ethoxylated sorbitan monolaurate, a wetting agent. Each of these solutions was diluted with 90 ml of water forming a 3,000 ppm suspension. Additional compositions having concentrations of 1,000, 500 and 200 ppm were prepared by further diluting the 3,000 ppm composition with water.

EXAMPLE 14

Rice Planthopper Foliar Test

One pot containing approximately 20 Mars variety rice seedlings was treated with each formulation at 1,000 ppm active concentration by spraying with a spray atomizer. One day after treatment plants were covered with a tubular cage and twenty adult rice delphacids, *Sogatodes oryzicola*, were transferred into each cage.

Controls were also provided by duplicating this treatment except that the active compounds were not applied. The controls, however, included the placement on the control rice seedling plants, twenty adult rice planthoppers. Five days after transferring, counts were made of the surviving planthoppers in each pot and percent control was estimated in accordance with testing procedures well established in the art. The results of the testing of rice planthoppers (RPH) are given in Table II.

For comparative purposes and to illustrate the unexpected activity of the compounds, Table IIa gives the results of similar tests using the following compound analogs which are outside of the scope of this invention:

A) 1-methylethyl 5-(3,6-dihydro-2,6-dioxo-4-methyl-1(2H)-pyrimidinyl)-2-methylbenzoate;
B) 5-bromo-1,6-dimethyl-3-phenyl-2,4(1H,3H)-pyrimidinedione; and
C) 6-methyl-3-phenyl-2,4(1H,3H)-pyrimidinedione.

TABLE II

| Cmpd. No. | Estimated % Control RPH |
|---|---|
| 1 | 100 |
| 2 | 100 |
| 3 | 50 |
| 4 | 100 |
| 5 | 30 |
| 6 | 25 |
| 7 | 35 |
| 8 | 25 |
| 9 | 100 |
| 10 | 40 |
| 12 | 35 |
| 13 | 35 |
| 14 | 30 |
| 15 | 100 |
| 16 | 35 |
| 18 | 60 |
| 19 | 55 |
| 20 | 85 |
| 21 | 30 |
| 22 | 80 |
| 23 | 70 |
| 24 | 100 |
| 25 | 50 |
| 26 | 25 |
| 27 | 95 |
| 28 | — |

TABLE IIa

| Compound | Compound Structure | Estimated % Control RPH |
|---|---|---|
| A | [structure] | 0 |
| B | [structure] | 0 |
| C | [structure] | 0 |

EXAMPLE 15

Rice Planthopper Systemic Test

Test formulations of the compound were prepared at 200 ppm by dissolving 0.01 gram of the compound to be tested in 5 ml of acetone and adding 45 ml of distilled water plus 2 drops of ethoxylated sorbitan monolaurate.

A 25 ml aliquot of each test solution was injected into the root zone of each pot with a hypodermic needle and syringe. Each pot held about 475 grams of moist soil. The resulting soil concentrations of each compound to be tested was 10 ppmsc (parts per million soil concentration). Each pot contained approximately 20 Mars variety rice seedlings, 8 days old from seed, when treated. One day after treatment the plants were covered with a tubular cage and ten adult rice delphacids, *Sogatodes oryzicola*, were transferred into each cage. Five days after transferring, counts were made of the surviving planthoppers in each pot and the adjusted percent control was calculated using Abbotts formula.

The results of the testing as adjusted percent control of rice planthoppers (RPH) are given in Table III.

TABLE III

| Cmpd. No. | Estimated % Control RPH |
| --- | --- |
| 1 | 100 |
| 2 | 100 |
| 4 | 100 |
| 9 | 100 |
| 5 | 100 |
| 27 | 95 |
| 24 | 84* |

*Tested at 1 ppmsc

EXAMPLE 16

Aphid Foliar Tests

Formulations were prepared at 500 ppm from stock solutions and used to treat tomato plants infested with green peach aphids (GPA), *Myzus persicae*. Percent control was estimated at six days post treatment (Table IV).

TABLE IV

| Cmpd. No. | Estimated % Control RPH |
| --- | --- |
| 1 | 80 |
| 2 | 83 |
| 4 | 75 |
| 9 | 65 |
| 15 | 100 |

In a like manner, compositions of Compound No. 1, having concentrations of 200 ppm where sprayed onto sorghum infected with caged greenbugs, *Schizaphis graminum*. A count of the surviving greenbugs made five day post treatment indicated greater than 99 percent control.

EXAMPLE 17

Mite Test

The stock solution of 3000 ppm was diluted to 1000 ppm. For each compound tested, primary leaves, one from each of two cowpeas (in one pot), were sprayed with an atomizer to thoroughly wet the foliage.

One day following treatment, groups of approximately 25 adult mites (*Tetranychus urticae* Koch) were transferred onto the upper surface of each leaf in areas created by the application of a circle of tree tanglefoot.

Five days following infestation with mites, the plants were examined for live mites remaining on the leaves. The percent control was estimated based on the number of mites surviving on the check plants.

The results of the testing of mites (MI) are given in Table V.

TABLE V

| Cmpd. No. | Estimated % Control RPH |
| --- | --- |
| 10 | 30 |
| 14 | 100 |

EXAMPLE 18

Nematode Test

The stock solution of 3000 ppm was diluted to 500 ppm. For each compound, 25 ml was drenched onto 500 grams of soil infested with root knot nematode (*Meloidogyne incognita*) eggs in a pot, for a soil concentration of 25 ppmsc.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table VI.

TABLE VI

| Cmpd. No. | Estimated % Control RPH |
| --- | --- |
| 6 | 100 |
| 15 | 100 |
| 27 | 50 |
| 17 | 50 |
| 18 | 50 |
| 19 | 70 |
| 20 | 100 |

With dilutions of 1000 ppm or lower, pesticidal activity of certain of the compounds has been evident under field conditions for other plant sucking insects such as *Empoasca fabae* (leafhopper), *Psylla pyricola* (psylla), and *Unaspis citri* (scale).

The above embodiments and examples are merely illustrative of the scope and spirit of the instant invention which is only limited by the appended claims.

We claim:

1. A compound of formula I:

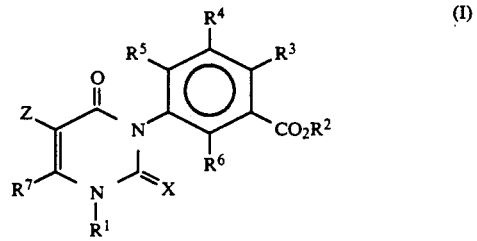

wherein $R^1$ is hydrogen, alkali or alkaline earth metal or organic base salts;

$R^2$ is i) hydrogen; alkali or alkaline metal salt; organic base salt; $C_1$-$C_6$ hydrocarbyl;

ii) —$RU_p$ wherein R is $C_1$-$C_6$ hydrocarbyl, U is halogen and p is an integer which cannot exceed the number of hydrogen atoms of the completely hydrogenated hydrocarbyl moiety;

iii) —$ROR^8$ wherein R is $C_1$-$C_6$ hydrocarbyl and $R^8$ is $C_1$-$C_4$ alkyl;

iv) 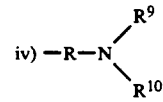

wherein R is $C_1$-$C_6$ hydrocarbyl and $R^9$ and $R^{10}$ are each independently hydrogen or $C_1$-$C_4$ alkyl;

v) —R—$CO_2R^{11}$ wherein R is $C_1$-$C_6$ hydrocarbyl and $R^{11}$ is $C_1$-$C_4$ alkyl;

vi) 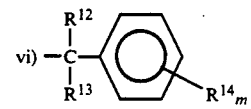

wherein $R^{12}$ and $R^{13}$ are each independently hydrogen, cyano or $C_1$-$C_2$ alkyl, $R_m^{14}$ is each independently for m of 1 to 5, $C_1$-$C_4$ alkyl, $C_1$-$C_4$ alkoxy, halo or nitro and m is 0,1,2,3,4 or 5;

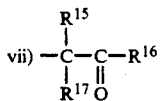

wherein $R^{15}$, $R^{16}$ and $R^{17}$ are each independently hydrogen or methyl; and

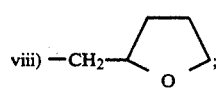

$R^3$ is $C_1$-$C_6$ hydrocarbyl, $C_1$-$C_6$ alkoxy, $C_1$-$C_6$ alkylthio or $C_3$-$C_6$ cycloalkyl;
$R^4$, $R^5$ and $R^6$ are each independently hydrogen, halogen, $C_1$-$C_4$ alkyl or $-CO_2R^{18}$ wherein $R^{18}$ is $C_1$-$C_4$ alkyl;
$R^7$ is $C_1$-$C_6$ halogenated hydrocarbyl;
X is oxygen or sulfur; and
Z is hydrogen or halogen.

2. A compound of claim 1 wherein:
$R^1$ is hydrogen or potassium;
$R^2$ is hydrogen or $C_1$-$C_6$ hydrocarbyl;
$R^3$ is $C_1$-$C_4$ alkyl, $C_1$-$C_4$ alkoxy or $C_1$-$C_4$ thioalkyl;
$R^4$, $R^5$ and $R^6$ are hydrogen;
$R^7$ is $C_1$-$C_3$ fluorinated alkyl;
X is oxygen; and
Z is hydrogen.

3. A compound of claim 1 wherein:
$R^1$ is hydrogen or potassium;
$R^2$ is ethyl methyl or isopropyl;
$R^3$ is methyl;
$R^4$, $R^5$ and $R^6$ are hydrogen;
$R^7$ trifluoromethyl;
X is oxygen; and
Z is hydrogen.

4. A composition having an activity selected from the group consisting of insecticidal, miticidal and nematocidal, which comprises:
A) an effective amount of compound of formula (I):

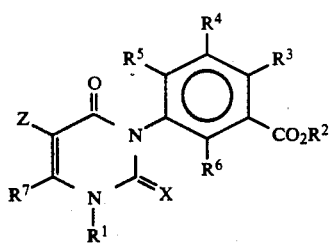

$R^1$ is hydrogen, alkali or alkaline earth metal or organic base salts;
$R^2$ is i) hydrogen; alkali or alkaline metal salt; organic base salt; $C_1$-$C_6$ hydrocarbyl;
i) $-RU_p$
wherein R is $C_1$-$C_6$ hydrocarbyl, U is halogen and p is an integer which cannot exceed the number of hydrogen atoms of the completely hydrogenated hydrocarbyl moiety;
iii) $-ROR^8$
wherein R is $C_1$-$C_6$ hydrocarbyl and $R^8$ is $C_1$-$C_4$ alkyl;

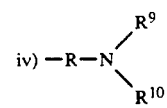

wherein R is $C_1$-$C_6$ hydrocarbyl and $R^9$ and $R^{10}$ are each independently hydrogen or $C_1$-$C_4$ alkyl;
v) $-R-CO_2R^{11}$
wherein R is $C_1$-$C_6$ hydrocarbyl and $R^{11}$ is $C_1$-$C_4$ alkyl;

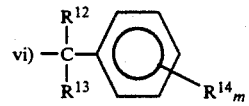

wherein $R^{12}$ and $R^{13}$ are each independently hydrogen, cyano or $C_1$-$C_2$ alkyl, $R_m^{14}$ is each independently for m of 1 to 5, $C_1$-$C_4$ alkyl, $C_1$-$C_4$ alkoxy, halo or nitro and m is 0,1,2,3,4 or 5;

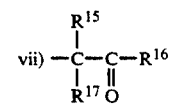

wherein $R^{15}$, $R^{16}$ and $R^{17}$ are each independently hydrogen or methyl; and

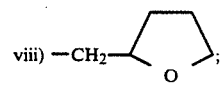

$R^3$ is hydrogen, halogen, nitro $C_1$-$C_6$ hydrocarbyl, $C_1$-$C_6$ alkoxy, $C_1$-$C_6$ alkylthio or $C_3$-$C_6$ cycloalkyl;
$R^4$, $R^5$ and $R^6$ are each independently hydrogen, halogen, $C_1$-$C_4$ alkyl or $-CO_2R^{18}$ wherein $R^{18}$ is $C_1$-$C_4$ alkyl;
$R^7$ is $C_1$-$C_6$ halogenated hydrocarbyl;
X is oxygen or sulfur; and
Z is hydrogen or halogen; and
B) a suitable carrier.

5. A composition according to claim 4 wherein
$R^1$ is hydrogen or potassium;
$R^2$ is hydrogen or $C_1$-$C_6$ hydrocarbyl;
$R^3$ is $C_1$-$C_4$ alkyl, $C_1$-$C_4$ alkoxy or $C_1$-$C_4$ thioalkyl;
$R^4$, $R^5$ and $R^6$ are hydrogen;
$R^7$ is $C_1$-$C_3$ fluorinated alkyl;
X is oxygen; and
Z is hydrogen.

6. A composition according to claim 4 wherein
$R^1$ is hydrogen or potassium;
$R^2$ is ethyl methyl or isopropyl;
$R^3$ is methyl;
$R^4$, $R^5$ and $R^6$ are hydrogen;
$R^7$ is trifluoromethyl;
X is oxygen; and
Z is hydrogen.

7. A method of controlling insects, mites and nematodes which comprises applying thereto an effective amount of the composition of claim 4.

8. A method of controlling insects, mites and nematodes which comprises applying thereto an effective amount of the composition of claim 5.

* * * * *